United States Patent [19]  [11] 4,204,079
Nelson  [45] May 20, 1980

[54] 2-DECARBOXY-2-HYDROXYMETHYL-CIS-4,5-DIDEHYDRO $PGF_1$ COMPOUNDS

[75] Inventor: Norman A. Nelson, Galesburg, Mich.

[73] Assignee: The Upjohn Company, Kalamazoo, Mich.

[21] Appl. No.: 923,770

[22] Filed: Jul. 12, 1978

Related U.S. Application Data

[60] Continuation of Ser. No. 778,649, Mar. 17, 1977, which is a division of Ser. No. 647,363, Jan. 8, 1976, Pat. No. 4,028,419.

[51] Int. Cl.$^2$ ............................................. C07C 177/00
[52] U.S. Cl. .................................................... 568/838
[58] Field of Search .......................................... 568/838

[56] References Cited

U.S. PATENT DOCUMENTS

| | | | |
|---|---|---|---|
| 3,878,239 | 4/1975 | Hayashi et al. | 562/503 |
| 3,914,282 | 10/1975 | Pike | 560/121 |
| 3,932,463 | 1/1976 | Schaub et al. | 560/121 |
| 3,933,889 | 1/1976 | Magerlein | 560/121 |
| 3,959,346 | 5/1976 | Schneidner | 560/121 |
| 3,962,293 | 6/1976 | Magerlein | 560/121 |
| 3,962,312 | 6/1976 | Hayashi et al. | 562/465 |

OTHER PUBLICATIONS

Burger, "Medicinal Chemistry," pp. 81–82 (1960).
Derwent Farmdec CPI No. 22,600 (British Patent 1,040,545-1-9-66).

*Primary Examiner*—Paul J. Killos
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

22 Claims, No Drawings

2-DECARBOXY-2-HYDROXYMETHYL-CIS-4,5-DIDEHYDRO PGF$_1$ COMPOUNDS

The present application is a continuation application of Ser. No. 778,649, filed Mar. 17, 1977; which is a divisional application of Ser. No. 647,363, filed Jan. 8, 1976, now U.S. Pat. No. 4,028,419.

The present invention relates to prostaglandin analogs, for which the essential material constituting disclosure therefor is incorporated by reference here from U.S. Pat. No. 4,028,419.

I claim:

1. A prostaglandin analog of the formula

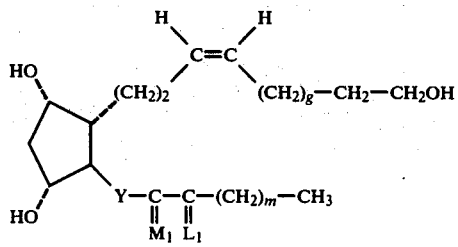

wherein Y is trans -CH=CH-;
wherein M$_1$ is

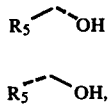

or

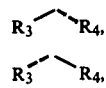

wherein R$_5$ is hydrogen or methyl;
wherein L$_1$ is $R_3 \diagup\!\!\diagdown R_4$, $R_3 \diagup\!\!\diagdown R_4$, or a mixture of $R_3 \diagup\!\!\diagdown R_4$ and $R_3 \diagup\!\!\diagdown R_4$, wherein R$_3$ and R$_4$ are hydrogen, methyl, or fluoro, the same or different, with the proviso that one of R$_3$ and R$_4$ is methyl only when the other is hydrogen or methyl;
wherein g is one, 2, or 3; and
wherein m is one to 5, inclusive.

2. A compound according to claim 1 wherein m is one or 2.

3. A compound according to claim 1, wherein m is 4 or 5.

4. A compound according to claim 1, wherein m is 3.

5. A compound according to claim 4, wherein g is one.

6. A compound according to claim 5, wherein at least one of R$_3$ and R$_4$ is fluoro.

7. A compound according to claim 6, wherein R$_3$ and R$_4$ are both fluoro.

8. A compound according to claim 7, wherein R$_5$ is hydrogen.

9. 2-Decarboxy-2-hydroxymethyl-cis-4,5-didehydro-16,16-difluoro-PGF$_{1\alpha}$, a compound according to claim 8.

10. 2-Decarboxy-2-hydroxymethyl-cis-4,5-didehydro-16,16-difluoro-15-epi-PGF$_{1\alpha}$, a compound according to claim 8.

11. A compound according to claim 5, wherein at least one of R$_3$ and R$_4$ is methyl.

12. A compound according to claim 11, wherein R$_3$ and R$_4$ are both methyl.

13. A compound according to claim 12, wherein R$_5$ is hydrogen.

14. 2-Decarboxy-2-hydroxymethyl-cis-4,5-didehydro-16,16-dimethyl-PGF$_{1\alpha}$, a compound according to claim 13.

15. 2-Decarboxy-2-hydroxymethyl-cis-4,5-didehydro-16,16-dimethyl-15-epi-PGF$_{1\alpha}$, a compound according to claim 13.

16. A compound according to claim 5, wherein R$_3$ and R$_4$ are both hydrogen.

17. A compound according to claim 16, wherein R$_5$ is methyl.

18. 2-Decarboxy-2-hydroxymethyl-cis-4,5-didehydro-15-methyl-PGF$_{1\alpha}$, a compound according to claim 17.

19. 2-Decarboxy-2-hydroxymethyl-cis-4,5-didehydro-15-epi-15-methyl-PGF$_{1\alpha}$, a compound according to claim 17.

20. A compound according to claim 16, wherein R$_5$ is hydrogen.

21. 2-Decarboxy-2-hydroxymethyl-cis-4,5-didehydro-PGF$_{1\alpha}$, a compound according to claim 20.

22. 2-Decarboxy-2-hydroxymethyl-cis-4,5-didehydro-15-epi-PGF$_{1\alpha}$, a compound according to claim 20.

* * * * *